United States Patent [19]

Santini

[11] Patent Number: 4,808,591

[45] Date of Patent: Feb. 28, 1989

[54] ANTIULCER 8-(2-PYRIMIDYLSULFINYL)QUINOLINES

[75] Inventor: Conrad Santini, Groton, Conn.

[73] Assignee: Pfizer Inc., New York, N.Y.

[21] Appl. No.: 156,371

[22] Filed: Feb. 16, 1988

[51] Int. Cl.$^4$ ..................... A61K 31/47; C07D 401/12
[52] U.S. Cl. ................. 514/274; 514/235.2; 544/122; 544/123; 544/300; 544/310; 544/317
[58] Field of Search ............... 544/300, 310, 317, 122, 544/123; 514/231, 274

[56] References Cited

FOREIGN PATENT DOCUMENTS 6015273  2/1981  Japan .................... 544/317

OTHER PUBLICATIONS

Minoru et al., Chemical Abstract 108-186740t.

Primary Examiner—Donald G. Daus
Assistant Examiner—Cecilia Shen
Attorney, Agent, or Firm—Peter C. Richardson; J. Trevor Lumb; James M. McManus

[57] ABSTRACT 8-(2-Pyrimidylsulfinyl)quinolines, inhibitors of the $H^+/K^{30}$ ATPase enzyme, are useful in the treatment of ulcers.

12 Claims, No Drawings

ANTIULCER 8-(2-PYRIMIDYLSULFINYL)QUINOLINES

BACKGROUND OF THE INVENTION

The present invention relates to antiulcer agents and, in particular, to a series of novel 8-(2-pyrimidylsulfinyl)-quinolines which are inhibitors of the H+/K+ ATPase enzyme. The present invention also includes a method for treating peptic ulcers in mammals, including man, a composition containing the therapeutic agents of this invention and intermediates leading to the final products.

Chronic gastric and duodenal ulcers, together known as peptic ulcers, are a common ailment for which a variety of treatments, including dietary measures, drug therapy and surgery, may be employed, depending on the severity of the condition. Particularly valuable therapeutic agents useful for the treatment of gastric hyperacidity and peptic ulcers are the histamine-$H_2$ receptor antagonists, which act to block the action of the physiologically active compound histamine at the $H_2$-receptor sites in the animal body and to thereby inhibit the secretion of gastric acid.

More recently, omeprazole, a 2-(pyridylmethylsulfinyl)benzimidazole and related compounds (*Drugs*, 32, 15 (1986) have been shown to be antiulcer agents, acting by a mechanism involving inhibition of the H+/K+ ATPase enzyme system.

8-Benzimidazole-thioalkyl-dihydro quinoline derivatives are reported in EPO application No. 239,129A to be antiulcer agents with acid suppressing and cytoprotection properties.

SUMMARY OF THE INVENTION

It has now been found that compounds of the following structure are potent inhibitors of the H+/K+ ATPase system and are useful antiulcer agents.

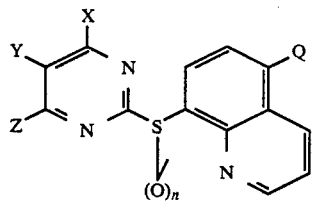

I or a pharmaceutically acceptable acid addition salt wherein n is 1, Q is hydrogen, fluoro, chloro, nitro, amino, trifluoromethyl, alkanoylamino of two to four carbon atoms, alkoxy of one to five carbon atoms, alkyl of one to five carbon atoms or dialkylamino said alkyl having one to four carbon atoms; X is hydrogen, alkyl of one to five carbon atoms or alkoxy of one to five carbon atoms; Y is hydrogen, fluoro, chloro, bromo, alkoxy of one to five carbon atoms or alkyl of one to five carbon atoms; and Z is hydrogen, alkyl of one to five carbon atoms, alkoxy of one to five carbon atoms, phenoxy, benzyloxy, cycloalkyloxy of five to seven carbon atoms, amino, alkylamino of one to four carbon atoms, dialkylamino said alkyl having one to four carbon atoms, anilino, N-alkylanilino said alkyl having from one to four carbon atoms; benzylamino, N-alkylbenzylamino said alkyl having from one to four carbon atoms, morpholino, piperidino or pyrrolidino.

Also part of the present invention are intermediates of formula I wherein n is 0.

In addition, the present invention includes a pharmaceutical composition for inhibiting gastric parietal cell H+/K+ ATPase in a mammal comprising a pharmaceutically acceptable carrier and a gastric parietal cell H+/K+ ATPase inhibiting amount of a compound of formula I where n is 1 and a method of treating gastric ulcers by inhibiting parietal cell H+/K+ ATPase in a mammalian subject in need of such treatment comprising administering to said subject a parietal cell H+/K+ ATPase inhibiting amount of a compound of formula I wherein n is 1.

A preferred group of compounds in this series are those of formula I where n is 1, Q and Y are each hydrogen and X is alkyl of one to five carbon atoms. Especially preferred within this group are those where X is methyl and Z is hydrogen, where X is methyl and Z is ethoxy and where X is methyl and Z is methyl.

A second group of preferred compounds are of formula I where n is 1, Q and Y are each hydrogen and X is alkoxy of one to five carbon atoms. Especially preferred is the compound where X is ethoxy and Z is hydrogen.

A third group of preferred compounds are of formula I where n is 1, X is hydrogen and Z is alkoxy of one to five carbon atoms. Especially preferred are the compounds where Y is methyl, Z is methoxy and Q is hydrogen and where Y is hydrogen, Z is ethoxy and Q is fluoro.

The present invention also embraces compounds of the formulae

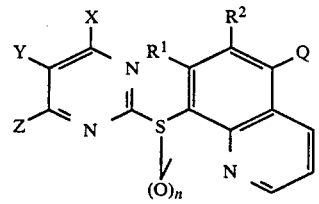

where n, X, Y, Z and Q are already defined, $R^1$ is fluoro and $R^2$ has the same definition as Q, and

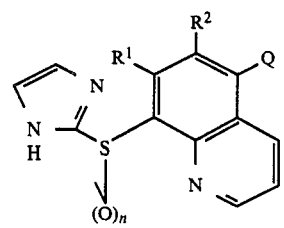

where n, $R^1$, $R^2$ and Q are defined.

DETAILED DESCRIPTION OF THE INVENTION

The antiulcer compounds of formula I wherein n is 1 are prepared by oxidation of the corresponding sulfide (n=0) using an appropriate oxidizing agent.

Those agents most useful are known oxidizing agents that can readily convert a sulfide to a sulfoxide. These include 30% hydrogen peroxide in a suitable solvent such as acetone or acetic acid, chromic anhydride, potassium permanganate, etc. The oxidizing agent of choice is m-chloroperbenzoic acid. This is particularly suitable since the product of the reaction is non-acidic and can readily be separated from either the per acid or acid by-product by simple aqueous base extraction of the latter.

This oxidation procedure using m-chloroperbenzoic acid is conduct in a reaction-inert solvent such as acetone, haloalkanes, aromatic hydrocarbons, tetrahydrofuran or ethyl acetate using one equivalent of oxidizing agent per equivalent of sulfide plus a slight excess of 10–25% to ensure complete oxidation, and about a five fold equivalent of sodium bicarbonate.

The reactants are combined at 0° C. and after the addition is complete the reaction allowed to warm to room temperature. Reaction time can vary depending on the structural nature of the sulfide. In general, several hours are required for completion of the reaction. The course of the reaction can be followed, if desired, by subjecting samples removed at various time intervals to simple thin-layer chromatography.

When the reaction is completed it is partitioned between an aqueous solution of sodium bicarbonate and a water immisible organic solvent, such as ethyl acetate. The product, which is isolated from the non-aqueous layer, can be purified by recrystallization or column chromatography.

The intermediate sulfides, which are also part of the present invention, are prepared by coupling a 2-halopyrimidine with an appropriate 8-mercaptoquinoline. In practice, equimolar amounts of the reactants are combined in a reaction-inert solvent, such as methanol containing one equivalent of an organic tertiary amine, such as triethylamine.

The reaction is conducted at ambient temperatures, the reaction time being about 12 to 24 hours. On completion, the reaction mixture can be added to water or an aqueous sodium bicarbonate solution and a water immiscible organic solvent. The product, on isolation from the organic layer, can be purified, if required, by recrystallization or column chromatography.

The pharmaceutically acceptable acid addition salts of the novel compounds of formula (I) are also embraced by the present invention. The salts are readily prepared by contacting the free base with an appropriate mineral or organic acid in either aqueous solution or in a suitable organic solvent. The solid salt may then be obtained by precipitation or by evaporation of the solvent. Especially preferred salts are the hydrochloride and maleate salts.

The utility of the present compounds as antiulcer agents is reflected in vitro by their inhibition of $H^+/K^+$ ATPase isolated from canine gastric mucosa. The enzyme activity was assayed according to Beil et al., *Brit. J. Pharmacol.* 82, 651–657 (1984) with slight modifications. The enzyme (1–2 micrograms) was preincubated at 37° C. for 45 minutes with a medium containing $2 \times 10^{-3}$M $MgCl_2$, 0.05M Tris-Cl buffer (pH 7.5) with or without 0.01M KCl, and the acid activated test drug in a final volume of 0.590 ml. The reaction was started by the addition of 0.010 mmol of ATP (final concentration $3 \times 10^{-3}$M). The reaction was terminated by adding trichloroacetic acid to a concentration of 4.2%. Liberated inorganic phosphate was determined using Fiske and Subbarow Reducer available commercially (e.g., from Sigma Chemical Co., P.O. Box 14508, St. Louis, MO 63178, U.S.A.). In this test the drugs are preferably first acid activated by incubating in 1:1 dimethylsulfoxide:0.02N HCl at 37° C. for 30 minutes.

The in vivo utility of the present compounds as antiulcer agents is also particularly shown by their cytoprotective activity. Such activity is demonstrated by the inhibition of ethanol-induced gastric ulceration in rats, using the method of Example 18 of U.S. Pat. No. 4,560,690.

The in vivo utility of the present compounds as antiulcer agents is, in part, reflected by their gastric antisecretory activity in rats by the following method:

A rat is placed in an ether jar until it has no blink reflex or pinch reflex (usually the rat is slightly cyanotic). The rat is then placed on its back, an ether cone is placed over its nose. It is important to monitor the coloring of the rat, and to remove the cone if the rat becomes excessively blue. With rat tooth forceps, the skin is lifted and an incision is made with small scissors from 2 cm below the sternum to the sternum. The muscle layer is cut in the same manner, exposing a view of the liver. The large lobe of the liver is gently lifted with straight smooth forceps exposing the pancreatic tissue and the intestine. The intestine is gently elevated and the pylorus sphincter is localized without touching the stomach. Curved forceps are carefully inserted beneath the pylorus. A length of silk thread (approximately 10 cm) is pulled through and snugly tied in a square knot. If the blood vessel is severed during the process, the rat is not used since the blood supply to the stomach will have been severely compromised under such conditions. An injection of drug or vehicle is made into the duodenum. The rat is lifted up by grasping above and below the incision, and the abdominal contents are gently inserted back into the cavity. The incision is closed with wound clips. Subsequent to stapling of wounds, rats are housed in show box cages with other surgerized rats, 4/cage. Within 15 minutes rats appear to be fully recovered from the ether anesthesia. They are carefully monitored for bleeding, which can occur if the staples are not properly positioned. Two hours after surgery the rat is sacrificed by i.p. injection of sodium pentabarbitol (1 ml/kg). Rat tooth forceps are used to lift the abdomen, and it is then cut open with dissecting scissors. The large lobe of the liver is lifted. The esophagus is located under the smaller lobe of the liver. Curved forceps are placed under the esophagus and it is lifted. A hemostat is used to clamp off the esophagus from the stomach and to gently cut the stomach free. In a funnel over a borosilicate tube, the stomach is cut along the greater curvature releasing the contents. The last of the contents is squeezed out. The fluid containing tubes are spun in the centrifuge at $3000\times$ rpm for 15 minutes at room temperature. The supernatants are carefully removed with pasteur pipettes, and placed in the graduated centrifuge tubes. Volumes are recorded. An automatic titrator (endpoint=pH 7.0) is used to determine pH and microequivalents of acid output/hr/100 g rat body weight. Results are reported as % inhibition of acid secretion in mg/kg.

For the treatment (prophylactic and therapeutic) of gastric ulcers in a mammalian subject by inhibiting gastric parietal cell $H^+/K^+$ ATPase, the products of the present invention are administered by a variety of conventional routes of administration including oral (with enteric coated devices) and parenteral. Preferably, the compounds are administered orally. In general, these compounds will be administered orally at doses between about 0.25 and 50 mg/kg body weight of the mammalian subject to be treated per day, preferably from about 0.5 to 30 mg/kg per day, in single or divided doses. If parenteral administration is desired, then these compounds can be given at total daily doses between about 0.2 and 20 mg/kg body weight of the mammalian subject to be treated. In a 100 Kg man, this translates to a daily oral dosage of about 25–5000 mg/day (preferably about 50–3000 mg/day) and a parenteral dosage of about 20–2000 mg/day. However, at the discretion of the attending physician, some variation in dosage will necessarily occur, depending upon the condition of the subject being treated and the particular compound employed.

When administered, the active ingredients will generally be further combined with pharmaceutically acceptable carriers or diluents. Suitable pharmaceutical carriers include inert diluents or fillers, sterile aqueous solutions and various organic solvents. The pharmaceutical compositions formed by combining the novel compounds of formula (I) or salts thereof and pharmaceutically acceptable carriers are readily administered in a variety of dosage forms such as tablets or capsules and the like. These pharmaceutical compositions can, if desired, contain additional ingredients such as flavorings, binders, excipients and the like. Thus, for oral administration, tablets containing various excipients, such as sodium citrate, are employed together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed as fillers in soft and hard filled gelatin capsules. Preferred materials therefor include lactose or milk sugar and high molecular weight polyethylene glycols.

Preferably, the products of this invention are administered orally in unit dosage form, i.e., as a single physically discrete dosage unit containing an appropriate amount of the active compound in combination with a pharmaceutically acceptable carrier or diluent. Examples of such unit dosage forms are tablets or capsules containing from about 5 to 1,000 mg of the active ingredient, the compound of formula (I) comprising from about 10% to 90% of the total weight of the dosage unit. As previously mentioned, the tablets or capsules used in oral administration should be enterically coated so that the active agent is released in the small intestine.

For parenteral administration, solutions or suspensions of the compounds of formula (I) in sterile aqueous solutions, for example aqueous propylene glycol, sodium chloride, dextrose or sodium bicarbonate solutions are employed. Such dosage forms are suitably buffered if desired. The preparation of suitable sterile liquid media for parenteral administration will be well known to those skilled in the art.

The present invention is illustrated by the following examples. However, it should be understood that the invention is not limited to the specific details of these examples. All temperatures are in degrees centigrade. Nuclear magnetic resonance spectra (NMR) were measured for solutions in deuterated chloroform (CDCl$_3$) deuterated methanol (CD$_3$OD) or deuterated dimethyl sulfoxide (DMSO-d$_6$), and peak positions are reported in parts per million downfield from tetramethylsilane. The following abbreviations for peak shapes are used: bs, broad singlet; s, singlet; d, doublet; t, triplet; q, quartet; m, multiplet.

EXAMPLE 1

8-(2-Pyrimidylsulfinyl)quinoline (I, n=1; X, Y, Z and Q=H)

To a solution of 5 ml. of tetrahydrofuran containing 170 mg. (0.71 m mole) of 8-(2-pyrimidylthio)quinoline was added 300 mg. of sodium bicarbonate and the mixture cooled to 0° C. m-Chloroperbenzoic acid (153 mg., 1.0 eg) in 5 ml. of the same solvent was added dropwise. After the addition was complete the reaction was allowed to warm to 25° C. and was stirred overnight. The reaction mixture was poured into a sodium bicarbonate solution and the product extracted with ethyl acetate. The organic layer was separated, dried over sodium sulfate and concentrated in vacuo. The residue was triturated with a small amount of ethyl acetate and filtered, 84 mg., m.p. 152°–155° C.

The NMR spectrum (300 MHz, CDCl$_3$) showed absorption at 8.86(dd, J=4.3, 1.6 Hz, 1H), 8.73(d, J=5.0 Hz, 2H), 8.48(dd, J=7.2, 1.2 Hz, 1H), 8.18 (dd, J=8.1, 1.5 Hz, 1H), 7.95(dd, J=8.3, 1.3 Hz, 1H), 7.76(dd, J=9.0, 7.2 Hz, 1H), 7.43(dd, J=8.2, 4.3 Hz, 1H) and 7.24(t, J=5.1 Hz, 2H)ppm.

EXAMPLE 2

8-(4-n-Propoxy-2-pyrimidylsulfinyl)-quinoline (I, n=1; X=n—C$_3$H$_7$O; Y, Z and Q=H)

To a mixture of 710 mg. (2.38 m mole) of 8-(4-n-propoxy-2-pyrimidylthio)quinoline and 999 mg. of sodium bicarbonate (11.9 m mole) in 40 ml. of methylene chloride cooled to 0° C. was added dropwise over a period of 15 minutes 574 mg. (3.33 m mole) of m-chloroperbenzoic acid in 15 ml. of the same solvent. The reaction mixture was stirred for 30 minutes and was then allowed to warm to room temperature and stirred overnight. The reaction was diluted with methylene chloride and the organic layer washed successively with a saturated sodium bicarbonate solution, water and a saturated brine solution. The organic phase was separated, dried over magnesium sulfate and concentrated to give 745 mg. of crude product which was purified by chromatographing on silica gel, 367 mg.

The NMR spectrum (300 MHz, CDCl$_3$) showed absorption at 8.85(dd, J=4.3, 1.6 Hz, 1H), 8.42(dd, J=7.2, 1.3 Hz, 1H), 8.38(d, J=5.5 Hz, 1H), 8.17(dd, J=8.1, 1.6 Hz, 1H), 7.92(dd, J=8.3, 1.4 Hz, 1H), 7.72(t, J=7.7 Hz, 1H), 7.4(dd, J=8.1, 4.0 Hz, 1H), 6.54(d, J=5.6 Hz, 1H), 4.0(m, 2H), 1.48(b, 2H) and 0.79(t, J=7.4 Hz, 3H)ppm.

EXAMPLE 3

Employing the general oxidation procedures of Example 1 or 2 and starting with the appropriate sulfide the following products were prepared

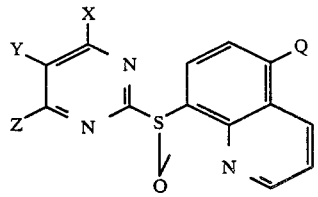

| X | Y | Z | Q | NMR(300MHz,ppm) |
|---|---|---|---|---|
| CH₃O | H | H | H | (CDCl₃) 8.87(dd, J=4.3, 2.3Hz, 1H), 8.45(dd, J=7.2, 1.5Hz, 1H), 8.4(dd, J=5.6, 1.1Hz, 1H), 8.19(dd, J=8.8, 2.1Hz, 1H), 7.95(d, J=8.3Hz, 1H), 7.75 (t, J=7.2Hz, 1H), 7.43(dd, J=8.4, 4.1Hz, 1H), 6.59(dd, J=6.0, 1.1Hz, 1H), 3.73(s, 3H). |
| φO | H | H | H | (CDCl₃) 8.7(dd, J=4.3, 1.7Hz, 1H), 8.59(d, J=6.1Hz, 1H), 8.31(dd, J=7.2, 1.3Hz, 1H), 8.15(dd, J=8.1, 1.6Hz, 1H), 7.9(dd, J=8.3, 1.3Hz, 1H), 7.66(dd, J=9.0, 7.7Hz, 1H), 7.38(dd, J=8.1, 4.3Hz, 1H), 7.13(m, 3H), 6.74(d, J=5.5Hz, 1H), 6.7(m,2H). |
| C₂H₅O | H | H | H | (CDCl₃) 8.85(dd, J=4.3, 1.7Hz, 1H), 8.42(d, J=5.3Hz, 1H), 8.38(d, J=5.5Hz, 1H), 8.17(dd, J=8.8, 1.7Hz, 1H), 7.92(bd, J=8.3Hz, 1H), 7.72(t, J=7.2Hz, 1H), 7.42(dd, J=8.8, 4.4Hz, 1H, 6.54(d, J=5.5Hz, 1H), 4.13(dq, J=6.8, 1.5Hz, 2H), 1.07(t, J=6.8Hz, 3H). |
| (CH₃)₂N | H | H | H | (CDCl₃) 8.88(dd, J=4.1, 1.4Hz, 1H), 8.4(dd, J=7.3, 1.6Hz, 1H), 8.14(dd, J=8.2, 1.7Hz, 1H), 8.1(d, J=6.4Hz, 1H), 7.87(dd, J=8.2, 1.4Hz, 1H), 7.68(t, J=7.8Hz, 1H), 7.39(dd, J=8.2, 4.3Hz, 1H), 6.19(d, J=6.4Hz, 1H), 2.84(bs, 6H). |
| φCH₂O | H | H | H | (CDCl₃) 8.86(dd, J=4.3, 1.9Hz, 1H), 8.46(m, 2H), 8.2(dd, J=8.5, 1.8Hz, 1H), 7.95(dd, J=8.3, 1.3Hz, 1H), 7.75(t, J=7.8Hz, 1H), 7.43(dd, J=8.1, 4.3Hz, 1H), 7.23-7.26(m, 3H), 7.14-7.17(m, 2H), 6.63(d, J=5.5Hz, 1H), 5.16(AB, J=12.2Hz, 2H). |
| CH₃O | H | CH₃O | H | (CDCl₃) 8.97(dd, J=4.3, 1.6Hz, 1H), 8.28(dd, J=7.2, 1.3Hz, 1H), 8.2(dd, J=8.1, 1.6Hz, 1H), 7.94(dd, J=7.7, 1.3Hz, 1H), 7.7(t, J=7.8Hz, 1H), 7.48(dd, J=8.3, 4.1Hz, 1H), 7.07 (s, 1H), 3.92(s, 3H), 3.66(s, 3H). |
| φNH | H | H | H | (CDCl₃) 8.91(dd, J=4.3, 1.6Hz, 1H), 8.43(dd, J=7.2, 1.4Hz, 1H), 8.18(dd, J=8.4, 1.9Hz, 1H), 8.12(d, J=5.8Hz, 1H), 7.94(dd, J=8.3, 1.4Hz, 1H), 7.73(t, J=7.8Hz, 1H), 7.57(bs, 1H), 7.42(dd, J=8.2, 4.3Hz, 1H), 7.06-7.24(m, 5H), 6.55(d, J=6.0Hz, 1H). |
| NH₂ | H | H | H | (DMSO-d₆) 8.81(dd, J=4.3, 1.6Hz, 1H), 8.47(dd, J=8.1, 1.3Hz, 1H), 8.17(d, J=8.4Hz, 1H), 8.17(d, J=7.4Hz, 1H), 7.96(d, J=6.0Hz, 1H), 7.86(dd, J=8.4, 7.3Hz, 1H), 7.59(dd, J=8.1, 4.3Hz, 1H), 7.3(bs, 2H), 6.35(d, J=6.0Hz, 1H). |
| CH₃ | H | CH₃ | H | (CDCl₃) 8.87(dd, J=4.3, 1.9Hz, 1H), 8.44(dd, J=7.2, 1.9Hz, 1H), 8.16(dd, J=8.2, 1.6Hz, 1H), 7.91(dd, J=8.0, 1.6Hz), 1H), 7.73(t, J=7.8Hz, 1H), 7.41(dd, J=8.1, 4.3Hz, 1H), 6.9(s, 1H), 2.40(s, 6H). |

-continued

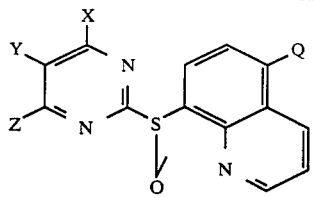

| X | Y | Z | Q | NMR(300MHz,ppm) |
|---|---|---|---|---|
| pyrrolidin-1-yl | H | H | H | (CDCl$_3$) 8.78(dd, J=4.3, 1.6Hz, 1H), 8.70(dd, J=7.2, 1.3Hz, 1H), 8.16(dd, J=8.2, 1.7Hz, 1H), 8.07(dd, J=7.9, 1.0Hz, 1H), 8.04(d, J=5.8Hz, 1H), 7.71(dd, J=8.3, 7.1Hz, 1H), 7.37(dd, J=8.2, 4.3Hz, 1H), 6.21(d, J=5.8Hz, 1H), 3.4(bt, J=5.9Hz, 2H), 3.27(bt, J=5.7Hz, 2H), 1.99(bq, J=6.1Hz, 2H), 1.84(bq, J=6.0Hz, 2H). |
| (C$_2$H$_5$)$_2$N | H | H | H | (CDCl$_3$) 8.9(dd, J=4.1, 1.9Hz, 1H), 8.42(dd, J=7.3, 1.3Hz, 1H), 8.10–8.19(m, 2H), 7.9(dd, J=8.3, 1.3Hz, 1H), 7.72(t, J=7.8Hz, 1H), 7.42(dd, J=8.5, 4.0Hz, 1H), 6.18(d, J=5.7Hz, 1H), 3.19(bq, J=7.2Hz, 4H), .65–.98(bm, 6H). |
| morpholin-4-yl | H | H | H | (DMSO-d$_6$) 8.82(dd, J=4.4, 1.9Hz, 1H), 8.47(dd, J=8.7, 1.7Hz, 1H), 8.19(dd, J=6.9, 1.6Hz, 1H), 8.14(d, J=6.5Hz, 1H), 7.86(dd, J=8.6, 6.9Hz, 1H), 7.58(dd, J=8.1, 4.3Hz, 1H), 6.77(d, J=6.3Hz, 1H), 3.48(m, 4H), 3.37(m, 4H). |
| piperidin-1-yl | H | H | H | (CDCl$_3$) 8.91(dd, J=4.3, 1.6Hz, 1H), 8.42(dd, J=7.2, 1.3Hz, 1H), 8.16(dd, J=8.2, 1.7Hz, 1H), 8.09(d, J=6.3Hz, 1H), 7.89(dd, J=8.4, 1.5Hz, 1H), 7.70(t, J=7.5Hz, 1H), 7.41(dd, J=8.5, 4.0Hz, 1H), 6.26(d, J=6.4Hz, 1H), 3.37(bt, J=5.3Hz, 4H), 1.55(bq, J=5.6Hz, 2H), 1.38(bs, 4H). |
| (n-C$_3$H$_7$)$_2$N | H | H | H | (CDCl$_3$) 8.87(dd, J=4.2, 1.2Hz, 1H), 8.42(dd, J=7.2, 1.6Hz, 1H), 8.16(m, 2H), 7.91(dd, J=7.8, 1.0Hz, 1H), 7.72(t, J=7.8Hz, 1H), 7.2(dd, J=8.2, 4.3Hz, 1H), 6.18(d, J=6.3Hz, 1H), 3.08(bsext., 4H), 1.84(bs, 2H), 1.46(bs, 2H), .84(bs, 3H), .50(bs, 3H). |
| C$_2$H$_5$O | H | CH$_3$ | H | (CDCl$_3$) 8.86(dd, J=4.2, 1.9Hz, 1H), 8.42(d, J=7.3Hz, 1H), 8.18(bd, J=8.2Hz, 1H), 7.92(d, J=7.7Hz, 1H), 7.73(t, J=7.8Hz, 1H), 7.42(dd, J=8.2, 4.1Hz, 1H), 6.37(s, 1H), 4.0(bq, J=7.0Hz, 2H), 2.43(s, 3H), .97(t, J=7.1Hz, 3H). |
| cyclohexyl-O | H | H | H | (CDCl$_3$) 8.85(dd, J=4.3, 1.7Hz, 1H), 8.43(m, 2H), 8.19(dd, J=8.2, 1.7Hz, 1H), 7.94(bd, J=7.2Hz, 1H), 7.75(t, J=7.1Hz, 1H), 7.43(dd, J=8.2, 4.3Hz, 1H), 6.51(d, J=6.2Hz, 1H), 4.63(bq, 1H), 1.35–1.6(m, 7H), 1.08–1.2(m, 3H). |
| H | H | H | Cl | (CDCl$_3$) 8.88(dd, J=4.3, 1.7Hz, 1H), 8.73(dd, J=5.0, 1.3Hz, 2H), 8.57(dd, J=8.3, 1.2Hz, 1H), 8.4(d, J=7.9Hz, 1H), 7.85(d, J=7.9Hz, 1H), 7.53(dd, J=8.4, 4.2Hz, 1H), 7.25(t, J=5.0Hz, 1H). |

-continued

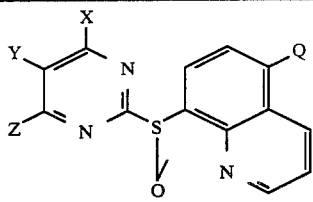

| X | Y | Z | Q | NMR(300MHz,ppm) |
|---|---|---|---|---|
| pyrrolidin-1-yl (N with ring) | H | CH₃ | H | (CDCl₃) 8.91(dd, J=4.3, 1.6Hz, 1H), 8.42(dd, J=7.6, 1.6Hz, 1H), 8.16(dd, J=8.4, 1.9Hz, 1H), 7.88(dd, J=8.4, 1.3Hz, 1H), 7.7(t, J=7.8Hz, 1H), 7.4(dd, J=8.1, 4.3Hz, 1H), 5.92(s, 1H), 3.12(bs, 4H), 2.33(s, 3H), 1.71–1.87(bm, 4H). |
| (CH₃)₂N | H | CH₃ | H | (CDCl₃) 8.9(dd, J=4.3, 1.9Hz, 1H), 8.42(dd, J=7.5, 1.8Hz, 1H), 8.16(dd, J=8.7, 1.9Hz, 1H), 7.89(dd, J=8.3, 1.4Hz, 1H), 7.7(t, J=7.6Hz, 1H), 7.4(dd, J=8.2, 4.3Hz, 1H), 6.06(s, 1H), 2.77(bs, 6H), 2.35(s, 3H). |
| CH₃ | H | H | H | (CDCl₃) 8.66(dd, J=4.3, 1.6Hz, 1H), 8.5(d, J=4.8Hz, 1H), 8.46(dd, J=7.2, 1.3Hz, 1H), 8.17(dd, J=8.8, 1.6Hz, 1H), 7.93(dd, J=8.3, 1.3Hz, 1H), 7.75(t, J=7.8Hz, 1H), 7.41(dd, J=8.2, 4.3Hz, 1H), 7.06(d, J=4.9Hz, 1H), 2.51(s, 3H). |
| C₂H₅ | H | CH₃ | H | (DMSO-d₆) 8.76(dd, J=4.0, 1.4Hz, 1H), 8.47(dd, J=8.5, 1.5Hz, 1H), 8.22(dd, J=7.3, 1.4Hz, 1H), 8.18(dd, J=7.9, 1.2Hz, 1H), 7.88(t, J=7.8Hz, 1H), 7.56(dd, J=8.1, 4.2Hz, 1H), 7.28(s, 1H), 2.56(q, J=7.5Hz, 2H), 2.36(s, 3H), .91(t, J=7.6Hz, 3H). |
| H | H | H | NO₂ | (DMSO-d₆) 8.84(m, 4H), 8.74(d, J=7Hz, 1H), 8.42(d, J=7Hz, 1H), 7.8(dd, J=7,4Hz, 1H), 7.6(t, J=8Hz, 1H). |
| CH₃ | H | CH₃ | NO₂ | (DMSO-d₆) 8.82(m, 2H), 8.64(d, J=7Hz, 8.34(d, J=7Hz, 1H), 7.78(dd, J=7,4Hz, 1H), 7.28(s, 1H), 2.3(s, 6H). |
| CH₃ | H | H | NO₂ | (CDCl₃) 8.92(dd, J=4,2Hz, 1H), 8.86(d, J=7Hz, 1H), 8.52(s, 2H), 8.42(d, J=7Hz, 1H), 7.6(dd, J=7,4Hz, 1H), 7.06(d, J=7Hz, 1H), 2.3(s, 3H). |
| CH₃O | CH₃ | H | H | (CDCl₃) 8.84(dd, J=4,2Hz, 1H), 8.42(dd, J=7,2Hz, 1H), 8.19(s, 1H), 8.15(dd, J=8,1Hz, 1H), 7.91(dd, J=8,1Hz, 1H), 7.71(t, J=8Hz, 1H), 7.4(dd, J=7,4Hz, 1H), 3.72(s, 3H), 2.02(s, 3H). |
| CH₃C(O)NH | H | H | H | (DMSO-d₆) 8.88(d, J=7Hz, 2H), 8.76(m, 1H), 8.64(d, J=Hz, 1H), 8.2(m, 2H), 7.6(m, 2H), 2.16(s, 3H). |
| H | H | H | F | (DMSO-d₆) 8.8(m, 2H), 8.5(d, J=7Hz, 1H), 8.2(m, 1H), 7.72(m, 2H), 7.64(dd, J=7,4Hz, 1H), 7.54(t, J=7Hz, 1H). |
| NH₂ | H | H | H | (DMSO-d₆) 8.86(d, J=7Hz, 2H), 8.7(m, 1H), 8.6(d, J=7Hz, 1H), 7.8(d, J=7Hz, 1H), 7.54(t, J=7Hz, 1H), 7.42(dd, J=7,4Hz, 1H), 6.84(d, J=7Hz, 1H), 6.72(s, 1H). |
| H | H | H | (CH₃)₂N | (DMSO-d₆) 8.79(d, J=7Hz, 2H), 8.5(d, J=5Hz, 1H), 8.44(dd, J=7,1Hz, 1H), 8.0(d, J=7Hz, 1H), 7.5(t, J=7Hz, 1H), 7.42(dd, J=7,4Hz, 1H), 7.26(d, J=7Hz, 1H), 2.9(s, 6H). |
| CH₃ | H | H | NH₂ | (DMSO-d₆) 8.76–8.66(m, 1H), 8.66–8.54(m, 2H), 7.75(d, J=8Hz, 1H), 7.49–7.34(m, 2H), 6.81(d, J=8Hz, 1H), 6.73(s, 2H), 2.49(s, 3H). |

-continued

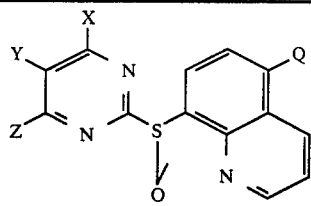

| X | Y | Z | Q | NMR(300MHz,ppm) |
|---|---|---|---|---|
| $CH_3$ | H | H | $CH_3\overset{O}{\underset{\|}{C}}NH$ | (DMSO-$d_6$) 10.27(s, 1H), 8.77(dd, J=4, 1Hz, 1H), 8.64(d, J=9Hz, 1H), 8.63(d, J=5Hz, 1H), 8.17(d, J=4Hz, 2H), 7.61(dd, J=9,4Hz, 1H), 7.44(d, J=5Hz, 1H), 2.48(s, 3H), 2.24(s, 3H). |
| $CH_3$ (maleate salt) | H | H | Cl | (CDCl$_3$) 8.84(d, J=3.7Hz, 1H), 8.6–8.65(m, 2H), 8.22(d, J=8.2Hz, 1H), 8.1(d, J=8.0Hz, 1H), 7.72(dd, J=8.6, 4.3Hz, 1H), 7.44(d, J=5.3Hz, 1H), 6.18(s, 2H), 2.46(s, 3H). |
| $CH_3$ (maleate salt) | H | $CH_3$ | Cl | (CDCl$_3$) 8.89(dd, J=4.3, 1.6Hz, 1H), 8.55(dd, J=8.5, 1.6Hz, 1H), 8.36(d, J=7.9Hz, 1H), 7.82(d, J=8.5Hz, 1H), 7.52(dd, J=8.4, 4.3Hz, 1H), 6.92(s, 1H), 6.35(s, 2H), 2.41(s, 6H). |
| $CH_3O$ | H | $CH_3$ | H | (CDCl$_3$) 8.87(dd, J=4.3, 1.6Hz, 1H), 8.43(dd, J=7.2, 1.3Hz, 1H), 8.18(dd, J=8.4, 1.9Hz, 1H), 7.93(dd, J=8.3, 1.3Hz, 1H), 7.73(t, J=7.8Hz, 1H), 7.42(dd, J=8.4, 4.3Hz, 1H), 6.4(s, 1H), 3.58(s, 3H), 2.42(s, 3H). |
| i-$C_3H_7O$ | H | H | H | (CDCl$_3$) 8.87(dd, J=4.3, 1.7Hz, 1H), 8.43(dd, J=7.3, 1.4Hz, 1H), 8.4(d, J=6.0Hz, 1H), 8.19(dd, J=8.5, 1.5Hz, 1H), 7.93(d, J=8.4Hz, 1H), 7.74(t, J=7.4Hz, 1H), 7.43(dd, J=8.6, 4.3Hz, 1H), 4.99(Sep, J=6.0Hz, 1H), 1.01(d, J=6.1Hz, 3H), .98(d, J=6.1Hz, 3H). |
| φ$CH_2$NH | H | H | H | (DMSO-$d^6$) 8.80(bd, J=4.3Hz, 1H), 8.47(dd, J=8.5, 1.5Hz, 1H), 8.21(d, J=5.6Hz, 1H), 8.19(dd, J=8.3, 1.5Hz, 1H), 8.05(d, J=8.2Hz, 1H), 7.87(t, J=8.0Hz, 1H), 7.59(dd, J=8.4, 4.2Hz, 1H), 7.18(bs, 3H), 6.88(bs, 2H); 6.45(d, J=5.7Hz, 1H), 4.13(b AB quart., 1H). |
| φN($CH_3$) | H | H | H | (DMSO-$d^6$) 8.84(dd, J=4.0, 1.4Hz, 1H), 8.49(dd, J=8.4, 1.5Hz, 1H), 8.21(d, J=5.9Hz, 1H), 8.18(t, J=3.9Hz, 1H), 8.08(d, J=6.4Hz, 1H), 7.87(t, J=7.8Hz, 1H), 7.60(dd, J=8.4, 4.1Hz, 1H), 7.42–7.28(m, 3H), 7.18(d, J=7.7Hz, 2H), 6.28(d, J=5.9Hz, 1H), 3.08(s, 3H). |
| φ$CH_2$N($CH_3$) | H | H | H | (DMSO-$d^6$) 8.75(bs, 1H), 8.40(bd, J=8.2Hz, 1H), 8.18(d, J=5.7Hz, 1H), 8.08(bd, J=8.1Hz, 1H), 7.79(bt, J=8.2Hz, 1H), 7.50(dd, J=8.3, 4.2Hz, 1H), 7.00–7.24(vbm, 3H), 6.50–6.80(vbm, 3H), 4.52(vbd, J=10.7Hz, 1H), 4.22(vbs, 1H), 2.81(s, 3H). |
| H | Cl | H | H | (DMSO-$d^6$) 8.75(dd, J=4, 2Hz, 1H), 8.47(dd, J=8, 2Hz, 1H), 8.25(d, J=7Hz, 1H), 8.22(d, J=7Hz, 1H), 7.89(t, J=8Hz, 1H), 7.83(s, 2H), 7.44(dd, J=4, 2Hz, 1H). |
| H | Br | H | H | (DMSO-$d^6$) 8.74(dd, J=4, 2Hz, 1H), 8.47(dd, J=8, 2Hz, 1H), 8.24(d, J=7Hz, 1H), 8.20(d, J=7Hz, 1H), 7.89(t, J=8Hz, 1H), 7.83(s, 2H), 7.56(dd, J=4, 2Hz, 1H). |
| $CH_3O$ | H | H | Cl | (CDCl$_3$) 8.89(dd, J=4.3, 1.7Hz, 1H, 8.57(dd, J=8.6, 1.7Hz, 1H), 8.38(d, J=5.5Hz, 1H), 8.37(d, J=7.9Hz, 1H), 7.83(d, J=7.9Hz, 1H), 7.53(dd, J=8.8, 4.3Hz, 1H), 6.60(d, J=5.5Hz, 1H), 3.76(s, 3H). |
| $C_2H_5O$ | H | H | Cl | (CDCl$_3$) 8.89(dd, J=4.1, 1.4Hz, 1H), 8.56(dd, J=8.8, 2.0Hz, 1H), 8.38(d, J=5.7Hz, 1H), 8.36(d, J=8.0Hz, 1H), 7.82(d, J=7.9Hz, 1H), 7.53(dd, J=8.6, 4.2Hz, 1H), 6.56(d, J=5.6Hz, 1H), 4.17(quart., J=7.0Hz, 2H), 1.12(t, |

-continued

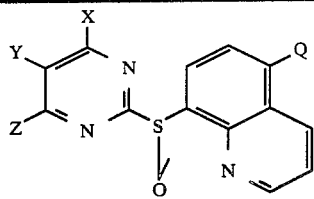

| X | Y | Z | Q | NMR(300MHz,ppm) |
|---|---|---|---|---|
| | | | | J=7.1Hz, 3H). |
| $CH_3$ | H | H | $(CH_3)_2N$ | (DMSO-$d^6$) 8.71(d, J=3.0Hz, 1H), 8.62(d, J=5Hz, 1H), 8.51(d, J=8Hz, 1H), 8.04(d, J=8Hz, 1H), 7.50(dd, J=8, 3Hz, 1H, 7.42(d, J=5Hz, 1H), 2.93(s, 6H), 2.48(s, 3H). |
| $CH_3$ | H | H | F | (DMSO-$d^6$) 8.85(d, J=4Hz, 1H), 8.62(d, J=5Hz, 1H), 8.56(d, J=9Hz, 1H), 8.22(dd, J=8, 6Hz, 1H), 7.74(dd, J=10, 8Hz, 1H), 7.67(dd, J=9, 4Hz, 1H), 7.44(d, J=5Hz, 1H), 2.46(s, 3H). |
| $CH_3O$ | H | $CH_3$ | Cl | (DMSO-$d^6$) 8.91(dd, J=4.3, 1.7Hz, 1H), 8.64(dd, J=8.8, 1.5Hz, 1H), 8.20(d, J=7.9Hz, 1H), 8.08(d, J=7.9Hz, 1H), 7.75(dd, J=8.7, 4.3Hz, 1H), 6.83(s, 1H), 3.52(s, 3H), 2.35(s, 3H). |
| $CH_3O(CH_2)_2O$ | H | H | H | (CDCl$_3$) 8.86(dd, J=4.1, 1.4Hz, 1H), 8.43(dd, J=7.2, 1.5Hz, 1H), 8.41(d, J=5.6Hz, 1H), 8.19(dd, J=8.5, 1.4Hz, 1H), 7.94(bd, J=7.8Hz, 1H), 7.74(t, J=7.4Hz, 1H), 7.43(dd, J=8.6, 4.2Hz, 1H), 6.64(d, J=5.5Hz, 1H), 4.26(sep., J=3.1Hz, 2H), 3.44(t, J=4.3Hz, 2H), 3.27(s, 3H). |
| $C_2H_5O$ | $CH_3$ | H | H | (DMSO-$d^6$) 8.86(dd, J=4, 2Hz, 1H), 8.43(dd, J=7, 2Hz, 1H), 8.22(s, 1H), 8.17(dd, J=9, 2Hz, 1H), 7.91(dd, J=8, 2Hz, 1H), 7.73(t, J=8Hz, 1H), 7.41(dd, J=9, 4Hz, 1H), 4.15(quart., J=7Hz, 2H), 2.02(s, 3H), 1.07(t, J=7Hz, 3H). |
| $C_2H_5O$ | H | $CH_3$ | Cl | (DMSO-$d^6$) 8.91(dd, J=4.1, 1.4Hz, 1H), 8.64(dd, J=8.8, 1.4Hz, 1H), 8.20(d, J=7.9Hz, 1H), 8.09(d, J=7.9Hz, 1H), 7.75(dd, J=8.8, 4.2Hz, 1H), 6.79(s, 1H), 3.90(quart., J=7.0Hz, 2H), 2.37(s, 3H), 0.85(t, J=6.9Hz, 3H). |
| $CH_3$ | H | $CH_3$ | $(CH_3)_2N$ | (DMSO-$d^6$) 8.74(d, J=4Hz, 1H), 8.50(d, J=8Hz, 1H), 7.99(d, J=8Hz, 1H), 7.50(dd, J=8, 4Hz, 1H), 7.28(d, J=8Hz, 1H), 7.27(s, 1H), 2.91(s, 6H), 2.35(s, 6H). |
| $CH_3$ | H | $CH_3$ | F | (DMSO-$d^6$) 8.87(d, J=5Hz, 1H), 8.56(d, J=8Hz, 1H), 8.20(dd, J=9, 6Hz, 1H), 7.74(dd, J=10, 9Hz, 1H), 7.68(dd, J=8, 5Hz, 1H), 7.30(s, 1H), 2.33(s, 6H). |
| H | $CH_3$ | H | H | (DMSO-$d^6$) 8.73(dd, J=4, 2Hz, 1H), 8.67(s, 2H), 8.46(dd, J=8, 2Hz, 1H), 8.25(d, J=8Hz, 1H), 8.19(d, J=9Hz, 1H), 7.90(t, J=8Hz, 1H), 7.56(dd, J=9, 4Hz, 1H), 2.23(s, 3H). |
| $CH_3$ | H | $CH_3$ | $\underset{CH_3CNH}{\overset{O}{\underset{\|}{}}}$ | (DMSO-$d^6$) 10.24(s, 1H), 8.79(dd, J=4, 1Hz, 1H), 8.63(dd, J=9, 1Hz, 1H), 8.16(d, J=2Hz, 1H), 7.59(dd, J=9, 4Hz, 1H), 7.28(s, 1H), 2.34(s, 3H), 2.22(s, 3H). |
| $CH_3$ | H | $CH_3$ | $NH_2$ | (DMSO-$d^6$) 8.74(d, J=4Hz, 1H), 8.60(d, J=8Hz, 1H), 7.70(d, J=8Hz, 1H), 7.41(dd, J=8, 4Hz, 1H), 7.24(s, 1H), 6.80(d, J=8Hz, 1H), 6.73(s, 2H), 2.36(s, 6H). |

PREPARATION A

8-(2-PYRIMIDYLTHIO)QUINOLINE

To a solution of 210 mg. (1.06 m mole) of quinoline-8-thiolhydrochloride in 5 ml. of dry methanol was added 128 mg. (1.05 m mole) of 2-chloropyrimidine in 2 ml. of the same solvent followed by 148 ul (1 m mole) of dry triethylamine. The reaction mixture was allowed to stir at room temperature overnight followed by the removal of the methanol in vacuo. The residue was partitioned between a saturated sodium bicarbonate solution and ethyl acetate. The organic phase was separated, dried and concentrated. The residue was redissolved in chloroform and concentrated without heat. The residue was triturated with ethyl acetate, filtered and dried, 170 mg., m.p. 165°-168° C.

PREPARATION B

Employing the procedure of Preparation A and staring with the appropriate starting materials, the following sulfides were prepared:

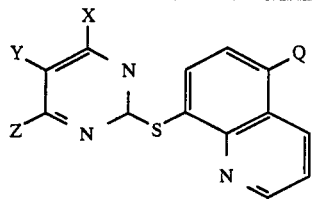

| X | Y | Z | Q |
|---|---|---|---|
| CH₃O | H | H | H |
| φO | H | H | H |
| C₂H₅O | H | H | H |
| φCH₂NH | H | H | H |
| (CH₃)₂N | H | H | H |
| φCH₂O | H | H | H |
| CH₃O | H | CH₃O | H |
| φNH | H | H | H |
| φN(CH₃) | H | H | H |
| φCH₂N(CH₃) | H | H | H |
| NH₂ | H | H | H |
| CH₃ | H | CH₃ | H |
| 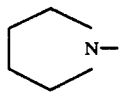 | H | H | H |
| n-C₃H₇O | H | H | H |
| (C₂H₅)₂N | H | H | H |
| morpholino-N— | H | H | H |
| piperidino-N— | H | H | H |
| (n-C₃H₇)₂N | H | H | H |
| CH₃ | H | C₂H₅O | H |
| cyclohexyl-O | H | H | H |
| H | H | H | Cl |
| | H | CH₃ | H |
| piperidino-N— | | | |
| (CH₃)₂N | H | CH₃ | H |
| CH₃ | H | H | H |
| H | Cl | H | H |
| CH₃ | H | C₂H₅ | H |
| H | H | H | NO₂ |
| CH₃ | H | CH₃ | NO₂ |
| CH₃ | H | H | NO₂ |
| CH₃O | CH₃ | H | H |
| H | H | H | NHCOCH₃ |
| H | H | H | F |
| H | H | H | NH₂ |

-continued

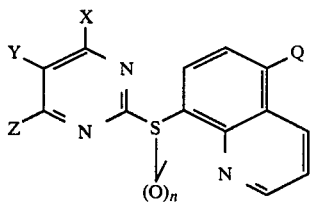

| X | Y | Z | Q |
|---|---|---|---|
| n-C₄H₉O | H | H | H |
| H | H | H | (CH₃)₂N |
| H | Br | H | H |
| CH₃ | H | H | NH₂ |
| CH₃ | H | H | Cl |
| CH₃ | H | H | NHCOCH₃ |
| CH₃ | H | CH₃ | Cl |
| CH₃ | H | CH₃O | H |
| i-C₃H₇O | H | H | H |
| CH₃O | H | H | Cl |
| C₂H₅O | H | H | Cl |
| CH₃ | H | H | (CH₃)₂N |
| CH₃ | H | H | F |
| CH₃ | H | CH₃ | Cl |
| CH₃O(CH₂)₂O | H | H | H |
| C₂H₅O | CH₃ | H | H |
| C₂H₅O | H | CH₃ | Cl |
| CH₃ | H | CH₃ | (CH₃)₂N |
| CH₃ | H | CH₃ | F |
| H | CH₃ | H | H |
| CH₃ | H | CH₃ | NHCOCH₃ |
| CH₃ | H | CH₃ | NH₂ |

I claim:
1. A compound of the formula

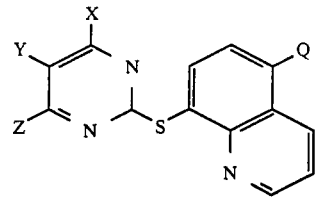

or a pharmaceutically acceptable acid addition salt thereof wherein Q is hydrogen, fluoro, chloro, nitro, amino, trifluoromethyl, alkanoylamino of two to four carbon atoms, alkoxy of one to five carbon atoms, alkyl of one to five carbon atoms or dialkylamino said alkyl having one to four carbon atoms; X is hydrogen, alkyl of one to five carbon atoms or alkoxy of one to five carbon atoms; Y is hydrogen, fluoro, chloro, bromo, alkoxy of one to five carbon atoms or alkyl of one to five carbon atoms; Z is hydrogen, alkyl of one to five carbon atoms, alkoxy of one to five carbon atoms, phenoxy, benzyloxy, cycloalkyloxy of five to seven carbon atoms, amino, alkylamino having one to four carbon atoms, dialkylamino said alkyl having one to four carbon atoms, anilino, N-alkylanilino said alkyl having one to four carbon atoms, benzylamino, N-alkylbenzylamino said alkyl having one to four carbon atoms, morpholino, piperidino or pyrrolidino; and n is an integer of 0 to 1.

2. A compound of claim 1, wherein Q and Y are each hydrogen, n is 1 and X is alkyl of one to five carbon atoms.

3. The compound of claim 2, wherein X is methyl and Z is hydrogen.

4. The compound of claim 2, wherein X is methyl and Z is ethoxy.

5. The compound of claim 2, wherein X is methyl and Z is methyl.

6. A compound of claim 1, wherein Q and Y are each hydrogen, n is 1 and X is alkoxy of one to five carbon atoms.

7. The compound of claim 6, wherein X is ethoxy and Z is hydrogen.

8. A compound of claim 1, wherein n is 1, X is hydrogen and Z is alkoxy of one to five carbon atoms.

9. The compound of claim 8, wherein Y is methyl, Z is methoxy and Q is hydrogen.

10. The compound of claim 8, wherein Y is hydrogen, Z is ethoxy and Q is fluoro.

11. A pharmaceutical composition for inhibiting gastric parietal cell $H^+/K^+$ ATPase in a mammal which comprises a pharmaceutically acceptable carrier and a gastric parietal cell $H^+/K^+$ ATPase inhibiting amount of a compound according to claim 1, wherein n is 1.

12. A method of treating gastric ulcers by inhibiting parietal cell $H^+/K^+$ ATPase in a mammalian subject in need of such treatment which comprises administering to said subject a parietal cell $H^+/K^+$ ATPase inhibiting amount of a compound according to claim 1, wherein n is 1.

* * * * *